(12) United States Patent
Shimuta

(10) Patent No.: US 12,290,387 B2
(45) Date of Patent: May 6, 2025

(54) COVER FOR ORAL INSTRUMENT

(71) Applicant: Murata Manufacturing Co., Ltd., Kyoto (JP)

(72) Inventor: Toru Shimuta, Kyoto (JP)

(73) Assignee: MURATA MANUFACTURING CO., LTD., Kyoto (JP)

(*) Notice: Subject to any disclaimer, the term of this patent is extended or adjusted under 35 U.S.C. 154(b) by 653 days.

(21) Appl. No.: 17/505,828

(22) Filed: Oct. 20, 2021

(65) Prior Publication Data
US 2022/0039899 A1   Feb. 10, 2022

Related U.S. Application Data

(63) Continuation of application No. PCT/JP2020/007908, filed on Feb. 27, 2020.

(30) Foreign Application Priority Data

May 20, 2019 (JP) .................. 2019-094553

(51) Int. Cl.
*A61B 50/00* (2016.01)
*A61B 5/0537* (2021.01)

(52) U.S. Cl.
CPC ............ *A61B 50/00* (2016.02); *A61B 5/0537* (2013.01); *A61B 2050/002* (2016.02)

(58) Field of Classification Search
None
See application file for complete search history.

(56) References Cited

FOREIGN PATENT DOCUMENTS

| JP | 2013-195118 A | 9/2013 |
| JP | 2018-186880 A | 11/2018 |
| WO | 2004/028359 A1 | 4/2004 |
| WO | WO2004028359 | * 4/2004 |
| WO | 2014/041585 A1 | 3/2014 |

OTHER PUBLICATIONS

International Search Report for International Patent Application No. PCT/JP2020/007908 dated May 26, 2020.

* cited by examiner

*Primary Examiner* — Yan Lan
(74) *Attorney, Agent, or Firm* — McDonald Hopkins LLC

(57) ABSTRACT

In a cover for covering a part of an oral instrument, a cover member is formed in a bag shape having an opening formed by partially bonding a measurement surface side sheet and an upper side sheet disposed to face each other. A protective sheet is bonded to the measurement surface side sheet of the cover member. The protective sheet protrudes from an opening edge of the cover member when viewed in a thickness direction of the cover member. Further, a bonded portion where the protective sheet and the cover member are bonded to each other is disposed along the opening edge of the cover member.

10 Claims, 2 Drawing Sheets

COVER FOR ORAL INSTRUMENT

CROSS REFERENCE TO RELATED APPLICATION

This is a continuation of International Application No. PCT/JP2020/007908 filed on Feb. 27, 2020 which claims priority from Japanese Patent Application No. 2019-094553 filed on May 20, 2019. The contents of these applications are incorporated herein by reference in their entireties.

BACKGROUND

Technical Field

The present disclosure relates to a cover for an oral instrument to be inserted into the oral cavity for use.

The oral instrument to be used by being inserted into the oral cavity as described in Patent Document 1 has a bar shape as a whole. When this type of oral instrument is used, an inserted portion of the oral instrument is covered with a cover member so as not to directly contact the oral cavity.

The cover member described in Patent Document 1 is formed in a bag shape having an opening formed by bonding three sides of a pair of rectangular sheets disposed to face each other. A protective sheet is bonded to one of the sheets of the cover member. Before using the oral instrument described in Patent Document 1, the cover member is attached to the oral instrument by inserting the oral instrument into the opening of the cover member. Then, the protective sheet is removed by peeling off the cover member from the protective sheet.

Patent Document 1: International Publication No. 2004/028359

BRIEF SUMMARY

When the oral instrument is inserted into the cover described in Patent Document 1, the oral instrument may be inserted into the opening of the cover member while being pressed against the protective sheet. In such a way of insertion, there is a concern that a tip end of the oral instrument may be inserted between the cover member and the protective sheet, and the cover may not be attached to the oral instrument.

In order to solve the above-described problem, an aspect of the present disclosure is to provide a cover for covering at least a part of an oral instrument to be used by being inserted into the oral cavity, the cover includes a cover member formed in a bag shape having an opening formed by partially bonding a pair of sheets disposed to face each other, and a protective sheet bonded to any one of the pair of sheets configuring the cover member, the protective sheet protrudes from an opening edge of the cover member when viewed in a thickness direction of the cover member, and a bonded portion where the protective sheet and the cover member are bonded to each other is disposed along the opening edge of the cover member.

According to the above-described configuration, due to the presence of the bonded portion disposed along the opening edge of the cover member, it is possible to suppress insertion of the oral instrument between the cover member and the protective sheet even in a case where a tip end of the oral instrument is inserted while being pressed against the protective sheet when the oral instrument is inserted into the opening of the cover member. As a result, the oral instrument can be easily inserted into the opening of the cover member.

According to one aspect of the present disclosure, it becomes easy to insert the oral instrument into the opening of the cover member.

DETAILED DESCRIPTION

Hereinafter, an embodiment of a cover for an oral instrument to be used by being inserted into the oral cavity will be described with reference to the drawings. First, an oral instrument 10 will be described.

Figure 1:
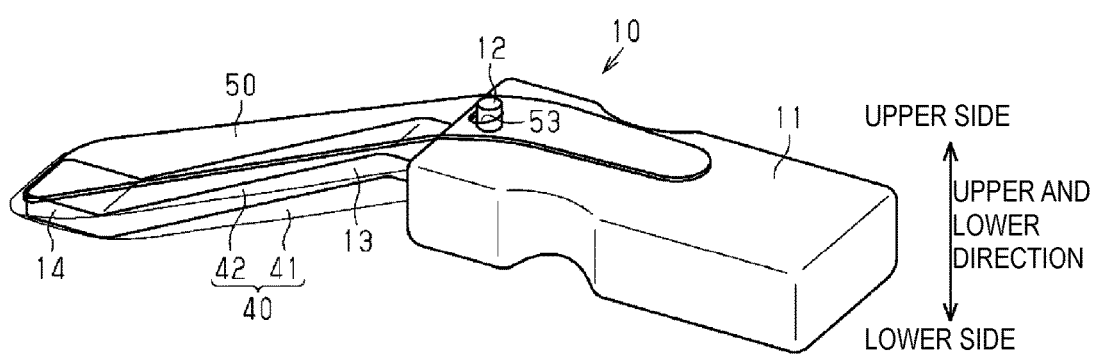
FIG. 1 is a perspective view illustrating a state in which a cover is attached to an oral instrument.

As illustrated in FIG. 1, the oral instrument 10 is a moisture content measuring instrument for measuring a moisture content in the oral cavity. The oral instrument 10 has a bar shape as a whole. In the oral instrument 10, substantially a half thereof at one side in a longitudinal direction is a grip portion 11 to be gripped by a user. The grip portion 11 has a substantially rectangular parallelepiped shape. A protruding portion 12 having a columnar shape protrudes from an upper side surface which is one of four surfaces along the longitudinal direction of the grip portion 11. Note that, in the following description, a protruding direction of the protruding portion 12 is referred to as an upper and lower direction, and a tip end side of the protruding direction of the protruding portion 12 is referred to as an upper side and the opposite side is referred to as a lower side.

An extending portion 13 extends along the longitudinal direction as a whole from an end surface at the other side in the longitudinal direction of the grip portion 11. The extending portion 13 has a flat prism shape. The extending portion 13 is thinner than the grip portion 11. The extending portion 13 extends so as to be inclined with respect to the longitudinal direction of the grip portion 11 such that the tip end side of the extending portion 13 is positioned more at the lower side than the end surface of the grip portion. A measurement unit 14 is connected to the tip end of the extending portion 13. The measurement unit 14 has a flat rectangular shape extending in the longitudinal direction of the grip portion 11.

Figure 2:
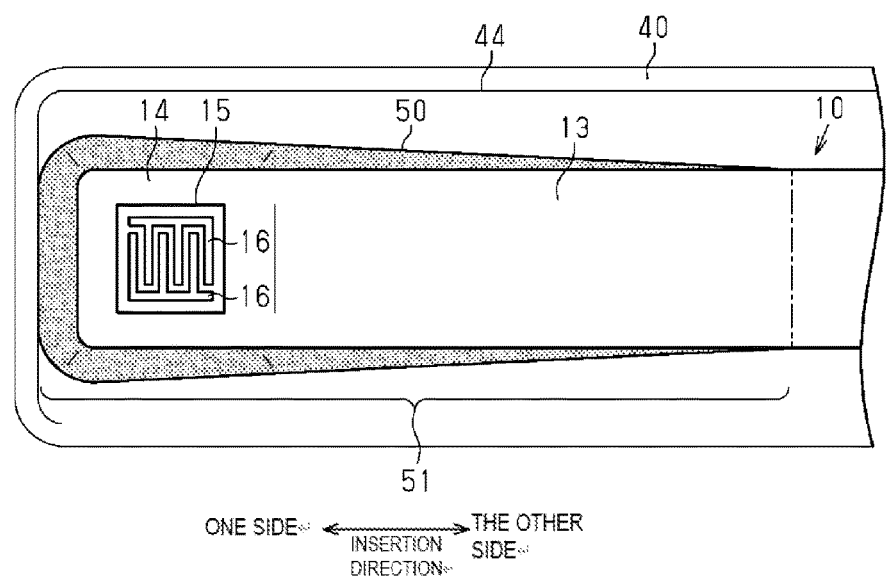
FIG. 2 is a partially enlarged bottom view of a measurement unit and the cover.

As illustrated in FIG. 2, a sensor 15 is attached to a lower surface of the measurement unit 14. The sensor 15 is an electrostatic capacity sensor in the present embodiment. The sensor 15 includes a pair of electrodes 16. The pair of electrodes 16 is arranged in a comb shape. The pair of electrodes 16 functions as electrodes of a capacitor. That is, a measurement target and liquid on the surface thereof facing the sensor 15 function as a dielectric for the pair of electrodes 16. Additionally, a capacitance value of the pair of electrodes 16 is a value corresponding to the measurement target and a moisture content of the surface thereof.

Although illustration is omitted, the oral instrument 10 incorporates a circuit board on which constituent members, such as an oscillation circuit, a control circuit, and the like are mounted. The oscillation circuit outputs a signal having a frequency corresponding to a capacitance value of the sensor. The control circuit detects the moisture content of the measurement target from the number of pulses of the output signal of the oscillation circuit. Then, a controller displays the detected moisture content on a display (not illustrated).

Next, a cover 20 applied to the oral instrument 10 will be described. Note that the cover 20 is a cover for covering the extending portion 13 and the measurement unit 14 of the oral instrument 10.

Figure 3:
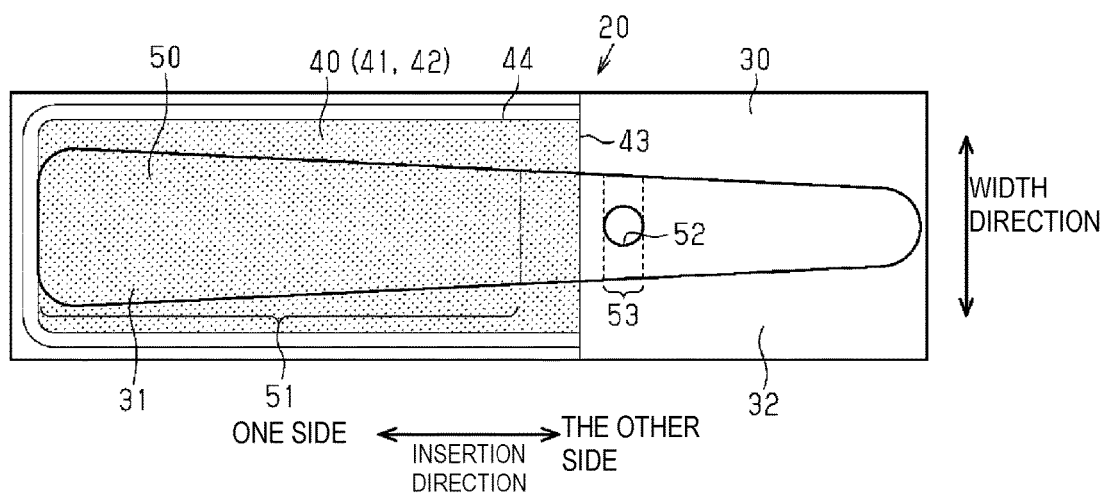
FIG. 3 is a top view of the cover.

As illustrated in FIG. 3, the cover 20 of the oral instrument 10 is configured to include a protective sheet 30, a cover member 40 bonded to the protective sheet 30, and a support member 50 bonded to the cover member 40. The protective sheet 30 has a rectangular shape when viewed in a thickness direction (a direction perpendicular to a main surface of the protective sheet 30). A material of the protective sheet 30 is polyethylene terephthalate (PET).

Figure 4:
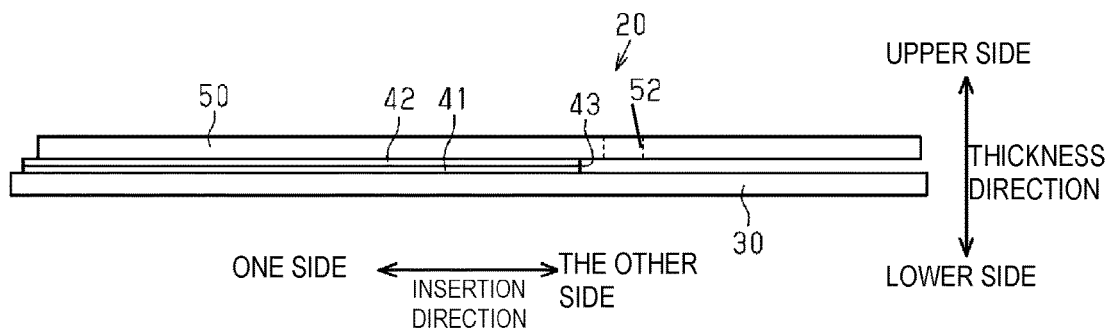
FIG. 4 is a side view of the cover.

As illustrated in FIG. 4, the cover member 40 is bonded to one surface of the protective sheet 30. The cover member 40 is configured of a measurement surface side sheet 41 having a substantially rectangular shape and an upper side sheet 42 having the same shape and size as the measurement surface side sheet 41. The measurement surface side sheet 41 and the upper side sheet 42 are overlapped with each other in a state in which the measurement surface side sheet 41 and the upper side sheet 42 are disposed to face each other. Additionally, as illustrated in FIG. 3, the measurement surface side sheet 41 and the upper side sheet 42 are bonded to each other by a closing portion 44 having a linear shape. The closing portion 44 extends along three sides of a short side at one side and long sides at both sides when viewed in a thickness direction of the measurement surface side sheet 41. As a result, among the sides of the measurement surface side sheet 41 and the upper side sheet 42, the short sides at the other side are not bonded and are opened. In addition, the cover member 40 configured of the measurement surface side sheet 41 and the upper side sheet 42 has a bag shape having an opening. In this embodiment, further, materials of the measurement surface side sheet 41 and the upper side sheet 42 are PET. Note that, as illustrated in FIG. 3, a direction along an opening edge 43 of the cover member 40, that is, a short side direction of the cover member 40 is defined as a width direction. In addition, a long side direction of the cover member 40 is defined as an insertion direction.

As illustrated in FIG. 4, thicknesses of the measurement surface side sheet 41 and the upper side sheet 42 are smaller than a thickness of the protective sheet 30. Further, the thickness of the measurement surface side sheet 41 is smaller than the thickness of the upper side sheet 42. In the present embodiment, the protective sheet 30 has a thickness of 75 micrometers, the measurement surface side sheet 41 has a thickness of 12 micrometers, and the upper side sheet 42 has a thickness of 25 micrometers.

As illustrated in FIG. 3, a dimension of the cover member 40 in the insertion direction is about 60% of a dimension of the protective sheet 30 in the insertion direction. Further, a dimension of the cover member 40 in the width direction is slightly smaller than a dimension of the protective sheet 30 in the width direction. That is, when viewed in the thickness direction of the measurement surface side sheet 41, a size of the cover member 40 is smaller than an outer shape of the protective sheet 30.

The cover member 40 is disposed within a range of the protective sheet 30. In other words, the cover member 40 is disposed so as not to protrude from the protective sheet 30. In this embodiment, when viewed in the thickness direction of the cover member 40, the cover member 40 is disposed at a position at one side in the insertion direction of the protective sheet 30. Thus, when viewed in the thickness direction of the cover member 40, the protective sheet 30 protrudes from the opening edge 43 of the cover member 40 toward the other side in the insertion direction.

A support member 50 having a sheet shape is attached to the upper side sheet 42 of the cover member 40.

Specifically, a surface at one side of the support member 50 is bonded to a surface opposite to a side of the upper side sheet 42 bonded to the measurement surface side sheet 41 in the thickness direction of the upper side sheet 42. In addition, all portions where the support member 50 and the measurement surface side sheet 41 face each other are bonded.

As illustrated in FIG. 4, a thickness of the support member 50 is larger than the thicknesses of the measurement surface side sheet 41 and the upper side sheet 42. In the present embodiment, the thickness of the support member 50 is 75 micrometers. Further, a material of the support member 50 is the same PET as the cover member 40.

As illustrated in FIG. 3, an outer shape of the support member 50 is substantially a trapezoidal shape when viewed in the thickness direction of the cover member 40. Specifically, a width dimension of the support member 50 gradually increases toward one side in the insertion direction of the support member 50 from the other side in the insertion direction of the support member 50. Additionally, as illustrated in FIG. 2, the maximum width dimension of the support member 50 is larger than a width dimension of the measurement unit 14 in the oral instrument 10 described above. In this embodiment, the width dimension of the support member 50 is the same as the width dimension of the measurement unit 14 of the oral instrument 10 at a substantially central position in the insertion direction of the support member 50. Thus, as indicated by dots in FIG. 2, a portion of the one side in the insertion direction from the center of the support member 50 is a wide width portion 51 that is larger than the width dimension of the measurement unit 14 of the oral instrument 10.

Additionally, as illustrated in FIG. 3, the maximum width dimension of the support member 50 is smaller than the width dimension of the cover member 40 and a width dimension of the protective sheet 30. As a result, a length of a portion of the support member 50 protruding from the opening edge 43 of the cover member 40 is smaller in the width direction than that of a portion of the protective sheet 30 protruding from the opening edge 43 of the cover member 40. Note that each corner of the support member 50 is chamfered in an arc shape.

A dimension of the support member 50 in the insertion direction is larger than the dimension of the cover member 40 in the insertion direction. Additionally, one end of the support member 50 in the insertion direction is positioned near a short side of the cover member 40 at one side in the insertion direction. Thus, the support member 50 protrudes from the opening edge 43 of the cover member 40 when viewed in the thickness direction of the cover member 40.

In the insertion direction of the support member 50, a through hole 52 having a circular shape penetrates at the other side from the opening edge 43 of the cover member 40. As a result, in the insertion direction of the support member 50, a range in which the through hole 52 is disposed is a deflection portion 53 having a bending rigidity smaller than that of other portions of the support member 50.

Here, a bonded portion between the protective sheet 30 and the cover member 40 will be described.

An adhesive layer, which is not illustrated, is interposed between the protective sheet 30 and the measurement surface side sheet 41 of the cover member 40. The protective sheet 30 and the measurement surface side sheet 41 of the cover member 40 are bonded to each other by the adhesive layer to form a bonded portion 31. Note that, in FIG. 3, the bonded portion 31 is indicated by dots.

On the protective sheet 30, there is a region where the adhesive layer is not provided. The region where the adhesive layer is not provided has an adhesive force of substantially zero. Thus, the region where the adhesive layer is not provided in the protective sheet 30 is a non-bonded portion 32 having an adhesive force smaller than that of the bonded portion 31. In the present embodiment, the adhesive force per 25 millimeters of the bonded portion 31 is smaller than 0.1 newton with respect to a target to be bonded made of PET.

The bonded portion 31 has a substantially rectangular shape when viewed in the thickness direction of the cover member 40. A position of an edge of the bonded portion 31 at the other side in the insertion direction coincides with that of the opening edge 43 of the cover member 40. That is, the bonded portion 31 is disposed along the opening edge 43 of the cover member 40. An edge of the bonded portion 31 at the one side in the insertion direction is positioned closer to the opening edge 43 side than an end of the cover member 40 at the one side in the insertion direction. In addition, both edges of the bonded portion 31 in the width direction are positioned closer to the center side of the cover member 40 in the width direction than both edges of the cover member 40 in the width direction.

A portion, of the surface of the protective sheet 30 at the cover member 40 side, where the bonded portion 31 described above is not disposed is the non-bonded portion 32. Specifically, all portions, of the surface of the protective sheet 30 at the cover member 40 side, that are positioned at outer side portions of an outer edge of the cover member 40 when viewed in the thickness direction of the protective sheet 30 are the non-bonded portion 32. That is, a portion, of the surface of the protective sheet 30 at the cover member 40 side, that protrudes from the opening edge 43 of the cover member 40 is the non-bonded portion 32. In addition, of the surface of the protective sheet 30 at the cover member 40 side, an outer edge portion along the four sides is the non-bonded portion 32.

Further, of the non-bonded portion 32, the edges of the non-bonded portion 32 in the width direction at the center side of the cover member 40 that are disposed at both sides of the bonded portion 31 in the width direction are positioned closer to the center side of the cover member 40 than the edges of the cover member 40 in the width direction. That is, edge portions at both sides in the width direction of the cover member 40 are not bonded to the protective sheet 30. In the present embodiment, the edges of the non-bonded portion 32 at the center side of the cover member 40 in the width direction are at the same positions as portions of the closing portion 44 that are positioned at sides of the long sides of the cover member 40.

Next, an operation of the present embodiment will be described.

First, the cover 20 is put on a desk, a palm, or the like such that the protective sheet 30 is positioned at the lower side. In this state, an end portion of the support member 50 at the other side in the insertion direction is gripped, and the support member 50 is separated from the protective sheet 30. Then, the upper side sheet 42 is separated from the measurement surface side sheet 41 together with the support member 50, and the opening of the cover member 40 is largely opened.

Next, the sensor 15 of the oral instrument 10 is directed downward and inserted into the inside of the cover member 40 while sliding on the portion of the protective sheet 30 protruding from the opening edge 43 of the cover member 40. Then, the oral instrument 10 is inserted into the cover member 40 until the tip end of the oral instrument 10 is positioned on the short side of the cover member 40 at the one side in the insertion direction. When the oral instrument 10 is inserted in this manner, a shape of an internal space of the cover member 40 becomes a pillar shape corresponding to a shape of the oral instrument 10. Thus, a part of the measurement surface side sheet 41 of the cover member 40 at each side in the width direction floats from the protective sheet 30.

After the oral instrument 10 is inserted into the cover member 40, as illustrated in FIG. 1, the protruding portion 12 of the oral instrument 10 is put in the through hole 52 of the support member 50. Thus, movement of the cover member 40 toward the tip end side of the oral instrument 10 is limited. Thereafter, the oral instrument 10 is lifted upward together with the cover member 40 while the protective sheet 30 is being pressed, and thus, the cover member 40 is peeled off from the protective sheet 30. As a result, only the measurement surface side sheet 41 of the cover member 40 is disposed on the surface of the oral instrument 10 facing the sensor 15, and measurement of the oral cavity by the sensor 15 becomes possible.

Next, effects of the present embodiment will be described.

(1) In the present embodiment, the bonded portion 31 between the cover member 40 and the protective sheet 30 is disposed along the opening edge 43 of the cover member 40. Thus, according to the present embodiment, even in a case where the tip end of the oral instrument 10 is inserted while being pressed against the protective sheet 30 when the oral instrument 10 is inserted into the opening of the cover member 40, the presence of the bonded portion 31 along the opening edge 43 suppresses insertion of the oral instrument 10 between the cover member 40 and the protective sheet 30. As a result, the oral instrument 10 can be easily inserted into the opening of the cover member 40.

(2) According to the present embodiment, the adhesive force per 25 millimeters of the bonded portion 31 is smaller than 0.1 newton. Thus, after the oral instrument 10 is inserted into the opening of the cover member 40, the cover member 40 can be easily peeled off without necessarily breaking or damaging the cover member 40.

(3) In the present embodiment, the thickness of the cover member 40 is correspondingly made thin so that the sensor 15 of the oral instrument 10 can be used. Thus, when the measurement surface side sheet 41 and the upper side sheet 42 are stuck and closed by static electricity or the like, it is difficult to separate the measurement surface side sheet 41 and the upper side sheet 42 from each other to open the opening only by deflecting the cover member 40. According to the present embodiment, the support member 50 is bonded to the upper side sheet 42 of the cover member 40, and the support member 50 protrudes from the opening edge 43 of the cover member 40 when viewed in the thickness direction of the cover member 40. Thus, since the upper side sheet 42 can be separated from the measurement surface side sheet 41 together with the support member 50 by separating the support member 50 and the protective sheet 30 from each other, the opening of the cover member 40 can be easily opened.

(4) According to the present embodiment, the thickness of the support member 50 is larger than the thicknesses of the measurement surface side sheet 41 and the upper side sheet 42 configuring the cover member 40, and the rigidity of the support member 50 is relatively large. In this way, by adopting a sheet having appropriate rigidity as the support member 50, the support member 50 can be easily gripped by fingers or the like. On the other hand, when the support member 50 is separated from the protective sheet 30, the support member 50 is bent at the deflection portion 53, and thus, it is possible to suppress an action of an excessive force on the cover member 40.

(5) In the present embodiment, a dimension of the support member 50 in the width direction is smaller than the dimension of the protective sheet 30 in the width direction, and the edge of the support member 50 does not coincide with the edge of the protective sheet 30. Thus, even when the support member 50 and the protective sheet 30 are in close contact with each other, the support member 50 can be easily separated from the protective sheet 30 with the edge of the support member 50 serving as a starting point.

(6) According to the present embodiment, the wide width portion 51 of the support member 50 has a width dimension larger than a width dimension of the tip end of the measurement unit 14 of the oral instrument 10. Additionally, a region, of the upper side sheet 42, to which the support member 50 is bonded has a double-layered structure with the support member 50, and bending or deflection is accordingly less likely to occur. Thus, when the support member 50 is separated from the protective sheet 30 to open the cover member 40, the region, of the upper side sheet 42, to which the support member 50 is bonded is less likely to be bent or deflected, and a dimension equal to or larger than the width dimension of the tip end of the oral instrument 10 is easily ensured as the width dimension of the internal space of the cover member 40. By ensuring a sufficient dimension as the width dimension of the internal space of the cover member 40 in this manner, the oral instrument 10 is unlikely to be caught in the cover member 40 when being inserted into the cover member 40, and can be quickly inserted. Furthermore, when the measurement surface side sheet 41 has many wrinkles in a state in which the oral instrument 10 is inserted into the cover member 40, there is a concern that the measurement accuracy of the sensor 15 may decrease. However, according to the present embodiment, since the width dimension of the wide width portion 51 is larger than the width dimension of the tip end of the measurement unit 14 of the oral instrument 10, the outer edge portion of the support member 50 can be deflected, and the wrinkles of the measurement surface side sheet 41 can be stretched by a force of returning the deflection.

(7) In the present embodiment, the portion of the protective sheet 30 protruding from the opening edge 43 of the cover member 40 is the non-bonded portion 32. In other words, a portion of the protective sheet 30 facing the support member 50 is the non-bonded portion 32. As a result, it is possible to prevent the support member 50 from not being separated from the protective sheet 30 due to bonding between the protective sheet 30 and the support member 50.

(8) In the present embodiment, not only the portion of the protective sheet 30 protruding from the opening edge 43 of the cover member 40 but also the outer edge portion of the protective sheet 30 protruding from the cover member 40 configure the non-bonded portion 32. Thus, according to the present embodiment, when a plurality of covers 20 are stacked and stored, it is possible to prevent the protective sheets 30 of the stacked covers 20 from being bonded to each other. As a result, even when a plurality of covers 20 are stacked and stored, the covers 20 can be easily taken out one by one.

(9) According to the present embodiment, since the entire cover member 40 is disposed within the range of the protective sheet 30, the measurement surface side sheet 41 that is a sheet being at the protective sheet 30 side in the cover member 40 is not exposed from the protective sheet 30. As a result, the measurement surface side sheet 41 having a high probability of coming into contact with the oral cavity during use of the oral instrument 10 can be kept clean.

(10) According to the present embodiment, portions that are not bonded to the protective sheet 30 are generated at the edge portions at both sides in the width direction of the cover member 40. Thus, after the oral instrument 10 is inserted into the cover member 40, the cover member 40 is gradually peeled off from the portion not bonded to the protective sheet 30 and is easily opened. That is, a case where the opening of the cover member 40 becomes difficult to be widely opened because the cover member 40 is bonded to the protective sheet 30 excessively firmly is unlikely to occur.

The above-described embodiment can be modified and implemented as follows. The present embodiment and the following modified examples can be implemented in combination in a range that there is no technical contradiction.

A position disposing the non-bonded portion 32 can be changed as appropriate. For example, the non-bonded portion 32 may be disposed only at an edge portion on at least one side in the width direction in a region where the protective sheet 30 and the cover member 40 face each other. Even in this case, after the oral instrument 10 is inserted into the cover member 40, the cover member 40 is easily opened while being gradually peeled off from a side of the non-bonded portion 32 that is not bonded to the protective sheet 30. In addition, the entire edge portions at both sides in the width direction of the cover member 40 may be bonded to the protective sheet 30.

The outer edge portion of the protective sheet 30 protruding from the cover member 40 may be the bonded portion 31. When an area of a portion of the protective sheet 30 protruding from the cover member 40 is small or an adhesive force of the bonded portion 31 is small, even in a case where the protective sheets 30 of the plurality of covers 20 are bonded to each other when the plurality of covers 20 are stacked, the covers 20 can be easily peeled off from each other.

When viewed in the thickness direction of the cover member 40, the outer shape of the protective sheet 30 may be the same as or smaller than the outer shape of the cover member 40. For example, the dimension of the protective sheet 30 in the width direction may be smaller than the dimension of the cover member 40 in the width direction. It is sufficient that at least a part of the protective sheet 30 protrude from the opening edge 43 of the cover member 40.

The portion of the protective sheet 30 protruding from the opening edge 43 of the cover member 40 may be the bonded portion 31. In the above embodiment, since the edge of the support member 50 does not coincide with the edge of the protective sheet 30, even when the support member 50 is bonded to the protective sheet 30, the support member 50 can be separated from the protective sheet 30 with the edge of the support member 50 serving as a starting point.

The wide width portion 51 may not be provided in the support member 50. That is, the width dimension of the support member 50 may be smaller than the width dimension of the measurement unit 14 of the oral instrument 10.

The width dimension of the portion of the protective sheet 30 protruding from the opening edge 43 of the cover member 40 may be the same as or smaller than a portion protruding from the width dimension of the portion of the support member 50 protruding from the opening edge 43 of the cover member 40.

The shape of the support member 50 is not limited to the example of the embodiment described above. For example, the shape may be a triangular shape or an elliptical shape instead of the trapezoidal shape in a plan view. Further, the support member 50 is not limited to have a sheet shape, and may have a string shape.

The materials of the support member 50, the cover member 40, and the protective sheet 30 are not limited to the examples of the embodiment described above. For example, the material of the support member 50 may be synthetic resin, such as polypropylene, polyethylene, nylon, polyvinyl chloride, or polyimide, or may be paper or nonwoven fabric. In addition, the support member 50 and the cover member 40 may be made of different materials. When the bending rigidity of the protective sheet 30 is small, there is a concern that the protective sheet 30 may buckle, and thus, it may be difficult to insert the extending portion 13 and the measurement unit 14. Because of this, the protective sheet 30 can be made of a material having a higher Young's modulus than that of the support member 50.

The dimension of the support member 50 in the insertion direction is not limited to the example of the embodiment described above. For example, the dimension of the support member 50 in the insertion direction may be longer than the dimension of the protective sheet 30 in the insertion direction.

The configuration of the deflection portion 53 of the support member 50 is not limited to the example of the embodiment described above. For example, the deflection portion 53 may be configured to be thinner than the other portions of the support member 50. Alternatively, the deflection portion 53 may be configured by bending a part of the support member 50 in a wave shape. That is, it is sufficient that the bending rigidity of the deflection portion 53 be smaller than that of the other portions of the support member 50. Further, the deflection portion 53 of the support member 50 may be omitted.

The arrangement of the support member 50 with respect to the cover member 40 is not limited to the example of the embodiment described above. For example, the end of the support member 50 at the one side in the insertion direction may be positioned at the center of the pair of short sides in the insertion direction of the cover member 40. It is sufficient that the support member 50 protrude from the opening edge 43 of the cover member 40 when viewed in the thickness direction of the cover member 40.

The adhesive force of the bonded portion 31 is not limited to the example of the embodiment described above. For example, the adhesive force per 25 millimeters of the bonded portion 31 may be equal to or larger than 0.1 newton, and may be determined in consideration of the entire area of the bonded portion 31, the strength of the cover member 40 and the protective sheet 30, and the like. However, from the viewpoint of peeling the cover member 40 from the protective sheet 30 with bare hands without necessarily using a tool, the adhesive force per 25 millimeters of the bonded portion 31 can be smaller than 1.0 newton.

The cover 20 may not be provided with the support member 50. For example, when the material of the measurement surface side sheet 41 and the upper side sheet 42 is a material that is less likely to be charged with static electricity, the opening of the cover member 40 is easily and widely opened by separating both sheets from each other without necessarily the support member 50.

The shape of the cover member 40 is not limited to the example of the embodiment described above. The shape of the cover member 40 may be a polygonal shape or an elliptical shape. Further, the cover member 40 may be provided with a "gusset" in the thickness direction of the cover member 40.

The number of openings of the cover member 40 may be plural. For example, the opening may also be present at the insertion side of the cover member 40, that is, at the side opposite to the opening edge 43. As described above, it is sufficient that the cover member 40 have a bag shape having at least one opening and capable of forming a space between the pair of sheets.

The size and arrangement of the closing portion 44 of the cover member 40 are not limited to the example of the present embodiment. For example, a length of the closing portion 44 in the width direction of the cover member 40 may be correspondingly large, and all the portions of the non-bonded portion 32 that are disposed at both sides of the bonded portion 31 in the width direction among the portions of the non-bonded portion 32 may be the closing portion 44.

The configuration of the pair of sheets in the cover member 40 is not limited to the example of the embodiment described above. For example, one sheet may be folded in two to configure a pair of sheets disposed to face each other. In this case, for example, the cover member 40 having a bag shape can be configured by bonding the edge portions of two sides of the sides that are not folded, of one sheet that is folded in two. In addition, for example, the pair of sheets may not have the same shape and size.

The shape of the protective sheet 30 is not limited to the example of the embodiment described above. For example, the shape of the protective sheet 30 may be a polygonal shape, a circular shape, or an elliptical shape. Additionally, the outer shape of the protective sheet 30 may not be larger than that of the cover member 40 when viewed in the thickness direction of the cover member 40.

The arrangement of the cover member 40 and the protective sheet 30 is not limited to the example of the embodiment described above. For example, the end of the protective sheet 30 at the one side in the insertion direction may be closer to the opening edge 43 than the end of the cover member 40 at the one side in the insertion direction.

The thickness of the protective sheet 30 may be the same as or larger than the thicknesses of the measurement surface side sheet 41 and the upper side sheet 42. Specifically, the thickness of the protective sheet 30 can be from 50 to 250 micrometers. In this case, since the rigidity of the protective sheet 30 is appropriately high, buckling of the protective sheet 30 is prevented when the oral instrument 10 is inserted while being pressed against the protective sheet 30, and thus, the oral instrument 10 is easily inserted into the cover member 40. For example, when the protective sheet 30 and the support member 50 are made of the same material, the thickness of the protective sheet 30 can be equal to or larger than the thickness of the support member 50, and the bending rigidity of the protective sheet 30 can be larger than the bending rigidity of the support member 50.

The thicknesses of the measurement surface side sheet 41 and the upper side sheet 42 are not limited to the example of the present embodiment. For example, the thickness of the measurement surface side sheet 41 may be smaller than the maximum thickness of a sheet through which the sensor 15 can make a measurement, and the thickness of the upper side sheet 42 may be larger than the thickness of the measurement surface side sheet 41. Specifically, in order to ensure the measurement accuracy of the oral instrument 10, the thickness of the measurement surface side sheet 41 can be from 5 to 20 micrometers. In addition, from the viewpoint of ease of handling of the cover member 40, the thickness of the upper side sheet 42 can be from 10 to 50 micrometers.

The thickness of the support member 50 may be the same as or smaller than the thicknesses of the measurement surface side sheet 41 and the upper side sheet 42. Specifically, from the viewpoint of ease of handling of the cover 20, the thickness of the support member 50 can be from 50 to 200 micrometers.

The arrangement of the bonded portion 31 is not limited to the example of the embodiment described above. It is sufficient that the bonded portion 31 be disposed at least on the surface at the upper side in the thickness direction of the protective sheet 30 along the opening edge 43 of the cover member 40. For example, the bonded portion 31 may be disposed only in a part along the opening edge 43, of a region where the protective sheet 30 and the cover member 40 face each other. Note that, depending on the adhesive layer configuring the bonded portion 31, manufacturing errors of the cover member 40 and the protective sheet 30, or the like, the edge of the bonded portion 31 may not coincide with the opening edge 43 of the cover member 40, and both of the edge of the bonded portion 31 and the opening edge 43 may be disposed at positions separated by several millimeters. As long as the difference due to such manufacturing errors or the like is slight, it can be said that the bonded portion 31 is disposed along the opening edge 43.

In addition, for example, even when the manufacturing errors or the like occur, the end of the bonded portion 31 at the other side in the insertion direction may be positioned closer to the one side in the insertion direction by several millimeters than the opening edge 43 of the cover member 40 so that the bonded portion 31 is not positioned in the portion of the protective sheet 30 protruding from the opening edge 43 of the cover member 40. As long as such a difference is slight, it can be said that the bonded portion 31 is disposed along the opening edge 43.

The configuration of the oral instrument 10 is not limited to the example of the embodiment described above. Any instrument may be applicable at least as long as the instrument is inserted into the oral cavity for use. Examples of such an oral instrument include thermometers and various dental jigs.

REFERENCE SIGNS LIST

10 ORAL INSTRUMENT
11 GRIP PORTION
12 PROTRUDING PORTION
13 EXTENDING PORTION
14 MEASUREMENT UNIT
15 SENSOR
16 ELECTRODE
20 COVER
30 PROTECTIVE SHEET
31 BONDED PORTION
32 NON-BONDED PORTION
40 COVER MEMBER
41 MEASUREMENT SURFACE SIDE SHEET
42 UPPER SIDE SHEET
43 OPENING EDGE
44 CLOSING PORTION
50 SUPPORT MEMBER
51 WIDE WIDTH PORTION
52 THROUGH HOLE
53 DEFLECTION PORTION

The invention claimed is:

1. A cover for covering at least a part of an oral instrument inserted into an oral cavity, the cover comprising:
   a cover member having a bag shape, the cover member comprising a pair of sheets facing each other and partially bonded to each other, the pair of sheets defining an opening where the pair of sheets are not bonded to each other; and
   a protective sheet comprising a bonded portion bonded to any one of the pair of sheets configuring the cover member, wherein
   the protective sheet comprises a protruding portion that protrudes from an opening edge of the cover member when viewed in a thickness direction of the cover member, wherein the protruding portion is a non-bonded portion that is devoid of adhesive,
   the bonded portion where the protective sheet and the one of the pair of sheets configuring the cover member are bonded to each other is disposed along the opening edge of the cover member,
   wherein a support member comprises an attached portion that is attached to another sheet of the pair of sheets configuring the cover member,
   the support member comprises a protruding portion that protrudes from the opening edge of the cover member when viewed in the thickness direction of the cover member, and
   when a direction along the opening edge of the cover member is defined as a width direction, the protruding portion of the protective sheet protruding from the opening edge of the cover member partially has a length in the width direction larger than a length of the protruding portion of the support member protruding from the opening edge of the cover member.

2. The cover for the oral instrument according to claim 1, wherein
   the bonded portion has an adhesive force per 25 millimeters being smaller than 1.0 newton.

3. The cover for the oral instrument according to claim 1, wherein
   the support member has a sheet shape,
   the support member and the cover member are made of the same material,
   a thickness of the support member is larger than a thickness of the cover member, and
   a part of the protruding portion of the support member protruding from the opening edge of the cover member is a deflection portion having a bending rigidity lower than a bending rigidity of another portion of the support member.

4. The cover for the oral instrument according to claim 1, wherein
   when the direction along the opening edge of the cover member is defined as the width direction, the attached portion of the support member attached to the cover member is provided with a wide width portion having a width dimension larger than a width dimension of a tip end at an insertion side of the oral instrument.

5. The cover for the oral instrument according to claim 2, wherein when viewed in a thickness direction of the cover member, an outer shape of the protective sheet is larger than an outer shape of the cover member, and the entire cover member is disposed within a range of the protective sheet.

6. The cover for the oral instrument according to claim 1, wherein when viewed in a thickness direction of the cover member, an outer shape of the protective sheet is larger than an outer shape of the cover member, and the entire cover member is disposed within a range of the protective sheet.

7. The cover for the oral instrument according to claim 3, wherein when viewed in a thickness direction of the cover member, an outer shape of the protective sheet is larger than an outer shape of the cover member, and the entire cover member is disposed within a range of the protective sheet.

8. The cover for the oral instrument according to claim 3, wherein when the direction along the opening edge of the cover member is defined as the width direction, the attached portion is provided with a wide width portion having a width dimension larger than a width dimension of a tip end at an insertion side of the oral instrument.

9. A cover for covering at least a part of an oral instrument inserted into an oral cavity, the cover comprising:

a cover member having a bag shape, the cover member comprising a pair of sheets facing each other and partially bonded to each other, the pair of sheets defining an opening where the pair of sheets are not bonded to each other; and a protective sheet comprising a bonded portion bonded to any one of the pair of sheets configuring the cover member, wherein the protective sheet comprises a protruding portion that protrudes from an opening edge of the cover member when viewed in a thickness direction of the cover member, the bonded portion where the protective sheet and the one of the pair of sheets configuring the cover member are bonded to each other is disposed along the opening edge of the cover member, when viewed in a thickness direction of the cover member, an outer shape of the protective sheet is larger than an outer shape of the cover member, and the entire cover member is disposed within a range of the protective sheet, and an outer edge portion of the protective sheet is a non-bonded portion having an adhesive force smaller than an adhesive force of the bonded portion.

10. A cover for covering at least a part of an oral instrument inserted into an oral cavity, the cover comprising:

a cover member having a bag shape, the cover member comprising a pair of sheets facing each other and partially bonded to each other, the pair of sheets defining an opening where the pair of sheets are not bonded to each other; and a protective sheet comprising a bonded portion bonded to any one of the pair of sheets configuring the cover member, the protective sheet comprises a protruding portion that protrudes from an opening edge of the cover member when viewed in a thickness direction of the cover member, and the bonded portion where the protective sheet and the one of the pair of sheets configuring the cover member are bonded to each other is disposed along the opening edge of the cover member, when viewed in the thickness direction of the cover member, an outer shape of the protective sheet is equal to or larger than an outer shape of the cover member, and the entire cover member is disposed within a range of the protective sheet, and when a direction along the opening edge of the cover member is defined as a width direction, a non-bonded portion having an adhesive force smaller than an adhesive force of the bonded portion is disposed at an edge portion on at least one side in the width direction in a region where the protective sheet and the cover member face each other.

* * * * *